United States Patent
Perner et al.

(10) Patent No.: US 9,751,850 B2
(45) Date of Patent: *Sep. 5, 2017

(54) TRPA1 ANTAGONISTS

(71) Applicant: AbbVie Inc., North Chicago, IL (US)

(72) Inventors: Richard J. Perner, Gurnee, IL (US); Michael E. Kort, Lake Bluff, IL (US); Stanley DiDomenico, Richmond, IL (US); Jun Chen, Lake Bluff, IL (US); Anil Vasudevan, Union Grove, WI (US)

(73) Assignee: ABBVIE INC., North Chicago, IL (US)

( * ) Notice: Subject to any disclaimer, the term of this patent is extended or adjusted under 35 U.S.C. 154(b) by 80 days.

This patent is subject to a terminal disclaimer.

(21) Appl. No.: 14/532,573

(22) Filed: Nov. 4, 2014

(65) Prior Publication Data
US 2015/0065538 A1 Mar. 5, 2015

Related U.S. Application Data

(63) Continuation of application No. 12/348,065, filed on Jan. 2, 2009, now Pat. No. 8,877,784.

(60) Provisional application No. 61/019,030, filed on Jan. 4, 2008.

(51) Int. Cl.
| | |
|---|---|
| *A61K 31/44* | (2006.01) |
| *A61K 45/06* | (2006.01) |
| *A61K 31/381* | (2006.01) |
| *C07D 333/22* | (2006.01) |
| *C07D 213/53* | (2006.01) |
| *C07D 215/12* | (2006.01) |
| *C07D 217/14* | (2006.01) |
| *C07D 333/20* | (2006.01) |
| *A61K 31/47* | (2006.01) |
| *A61K 31/472* | (2006.01) |
| *C07D 213/61* | (2006.01) |
| *C07D 213/64* | (2006.01) |

(52) U.S. Cl.
CPC .......... *C07D 333/22* (2013.01); *A61K 31/381* (2013.01); *A61K 31/44* (2013.01); *A61K 31/47* (2013.01); *A61K 31/472* (2013.01); *A61K 45/06* (2013.01); *C07D 213/53* (2013.01); *C07D 213/61* (2013.01); *C07D 213/64* (2013.01); *C07D 215/12* (2013.01); *C07D 217/14* (2013.01); *C07D 333/20* (2013.01)

(58) Field of Classification Search
CPC ...... A61K 31/381; A61K 31/44; A61K 31/47; A61K 31/472; A61K 45/06; C07D 215/12; C07D 217/14; C07D 333/20; C07D 333/22; C07D 213/53; C07D 213/61; C07D 213/64
USPC ........ 514/307, 311, 351, 357, 438; 546/145, 546/176, 300, 338; 549/75
See application file for complete search history.

(56) References Cited

FOREIGN PATENT DOCUMENTS

| | | |
|---|---|---|
| JP | 09040605 A2 | 2/1997 |
| WO | 03051841 A2 | 6/2003 |
| WO | 2007098252 A2 | 8/2007 |

OTHER PUBLICATIONS

Story G. M. et al., "Numbering the senses: role of TRPA1 in mechanical and cold sensation," Neuron, 50(2):177-180 (2006).
Story G. M. et al., "The Emerging Role of TRP Channels in Mechanisms of Temperature and Pain Sensation," Current Neuropharmacology, 4(3):183-196 (2006).
Story M. Gina, "ANKTM1, a TRP-like Channel Expressed in Nociceptive Neurons, is Activated by Cold Temperatures," Cell, 112:819-829 (2003).
Suwinski, "Database Beilstein Beilstein Institute for Organic Chemistry, Frankfurt-Main, DE: 1967, Troszkiewicz; Reader ID 7162062, XP002514996," (1967).
Tabakova, Svoboda et al., "Database CA (Online) Chemical Absracts Service, Columbus, Ohio, US; 1999: Anticandidial effect of phenylbutene derivatives and their interaction with ergosterol" XP002514989 retrieved from STN Database accession No. 1999:157.
Trevisani M. et al., "4-Hydroxynonenal, an endogenous aldehyde, causes pain and neurogenic inflammation through activation of the irritant receptor TRPA1," Proceedings of the National Academy of Sciences USA, 104 (33):13519-13524 (2007).
Unterhalt, B., "Ober das optische Verhalten isomerer Oxime, Archiv Der Pharmazie, XP002518708 ISSN: 0376-0367," 299(7):626-633 (1996).
Unterhalt, B., "(Dichlorophenyl) alkenones and their oximes, XP002514986 ISSN: 0365-6233," Archiv Der Pharmazie, 311(3):262-267 (1978).
Unterhalt, B. et al., "Ungesattigte Oxime, 14. Mitt. Halogensubsituierte 4-Phenyl-3-buten-2-on-oxime, Archiv Der Pharmazie, XP002518707 Weinheim, Germany ISSN: 0365-6233," 310(10):787-792 (1977).
Unterhalt et al., "Database Beilstein Beilstein Institute for Organic Chemistry, Frankfurt-Main, DE: Jun. 29, 1989, Beilstein RN 1939718, XP002514992," (1989).
Suwinski, "Database Beilstein Beilstein Institute for Organic Chemistry, Frankfurt-Main, DE; 1967: Beilstein RN 2266114, XP002514994," (1967).

(Continued)

*Primary Examiner* — Uma Ramachandran
(74) *Attorney, Agent, or Firm* — McAndrews, Held & Malloy, Ltd.

(57) ABSTRACT

Compounds of formula (I)

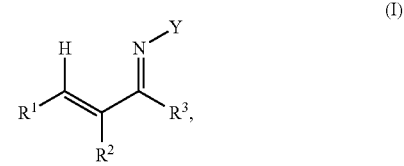

wherein $R^1$, $R^2$, $R^3$, and Y are defined in the description are TRPA1 antagonists. Compositions comprising such compounds and methods for treating conditions and disorders using such compounds and compositions are also disclosed.

4 Claims, No Drawings

(56) References Cited

OTHER PUBLICATIONS

Unterhalt et al., "Database Beilstein Beilstein Institute for Organic Chemistry, Frankfurt-Main, DE; Oct. 13, 2007: Beilstein RN 2050551, XP002514993," (2007).

Williams J. Michael et al., "A New General Method for Preparation of N. Methoxy-N-Methylamides Application in Direct Conversation of an Ester to a Ketone," Tetrahedron Letters, Elsevier Science Ltd., 36(31):5461-5464 (1995).

Williams et al., "Foye's Principles of Medicinal Chemistry," Fifth Edition, pp. 59-64, (2002).

Xu, Haoxing et al., "Oregano, thyme and clove-derived flavors and skin sensitizers activate specific TRP channels," Nature Neuroscience, 9(5):628-635 (2006).

Yin, Lunxiang et al., "Carbon-Carbon Coupling Reactions Catalyzed by Heterogeneous Palladium Catalysts," Chem. Rev., 107:133-173 (2007).

Yuan, Cheng-Yeh et al., Database CA (Online) Chemical Abstracts Service Columbus, Ohio, US: Chemotherapy of cancer. IV. Synthesis of .beta.-(5-substituted-2-thienyl)alanine and some of its derivatives, XP002518712 retrieved from STN Database accession, (1959).

Zurborg, Sandra et al., "Direct activation of the ion channel TRPA1 by Ca2+," Nature Neuroscience, 10(3):277-279 (2007).

International Preliminary Report on Patentability for PCT/US2009/030006 dated Jul. 15, 2010.

Banker, Gilbert S. et al., Modern Pharmaceutics, Marcel Dekker, New York, p. 596 (1996).

Wolff, Manfred E., "Burger's Medicinal Chemistry and Drug Discovery," Principles and Practice, John Wiley & Sons, 1(5):975-977 (1995).

West, Anthony R., "Solid State Chemistry and Its Applications," Wiley, New York, pp. 358 & 365 (1988).

Adam, Waldemar et al., "Control of Regioselectivity by the lone Substituent through Steric and Electronic Effects in the Nitrosoarene Ene Reaction of Deuterium-Labeled Trisubstituted Alkenens," J. Org. Chem, 67(24):8395-8399 (2002).

Andre, Eunice et al., "Cigarette smoke-induced neurogenic inflammation is mediated by a β-unsaturated aldehydes and the TRPA1 receptor in rodents," The Journal of Clinical Investigation, 118(7):2574-2582 (2008).

Smith, "Datbase Beilstein Beilstein Institute for Organic Chemistry, Frankfurt-Main, DE: 1979: Beilstein RN 2266114, XP002514995," (1979).

Bandell, Michael et al., "Noxious Cold Ion Channel TRPA1 is Activated by Pungent Compounds and Bradykinin," Neuron, 44:849-857 (2004).

Basha, A., "A Mild, General Method for Conversion of Esters to Amides," Tetrahedron Letters, Pergamon Press, 48:4171-4174 (1977).

Bautista M. Diane et al., "Pungent products from garlic activate the sensory ion channel TRPA1," PNAS, 102(34) 12248-12252 (2005).

Bautista M. Diane et al., "TRPA1 Mediates the Inflammatory Actions of Environmental Irritants and Proalgesic Agents," Cell, Elsevier Inc., 124:1269-1282 (2006).

Berge, S.M. et al., "Pharmaceutical Salts," J Pharmaceutical Sciences, 66:1-19 (1977).

Bessac F. Bret et al., "TRPA1 is a major oxidant sensor in murine airway sensory neurons," The Journal of Clinical Investigation, 118(5):1899-1910 (2008).

Chen Jun et al., Utility of Large-Scale Transiently Transfected Cells for Cell-Based High-Throughput Screens to Identify Transient Receptor Potential Channel A1 (TRPA1) Antagonists, "Journal of Biomolecular Screening," SAGE, 12(1)61-69 (2007).

Corey D.P. et al., "TRPA1 is a candidate for the mechanosensitive transduction channel of vertebrate hair cells," Nature, 432:723-730 (2004).

Dai Y. et al., "Sensitization of TRPA1 by PAR2 contributes to the sensation of inflammatory pain," Journal of Clinical Investigation, 117:1979-1987 (2007).

Database Registry Chemical Abstracts Service, Columbus, Ohio, US; 2004, XP002518713 Database accession No. RN 683222-72-2.

Database Registry Chemical Abstracts Service, Columbus, Ohio, US: 2004, XP002518714 Database accession No. RN 683222-75-5.

Dimmock J.R. et al., Chemical Abstracts Service, Columbus, Ohio, US; 1982, Synthesis and evaluation of some alkoxy-chloro-, and acyloxy-conjugated styrl ketones against P-388 lymphocytic leukemia and an examination of the metabolism and toxicologic.

Diogenes A. et al., "NGF up-regulates TRPA1:implications for orofacial pain," Journal of Dental Research, 86 (6):550-555 (2007).

Dornow, A. et al., "The description of substances similar to papavarine. II, con, XP002514987 ISSN:0376-0367," Archiv Der Pharmazie Und Berichte Der Deutschen Pharmazeutischen Gesellschaft, 22 (10):463-471 (1952).

Egorova V.S. et al., "Database Ca (Online) Chemical Abstracts Service, Columbus, Ohio, US: 2-Thiophene carboxaldehyde and its derivatives XP002518710 retrieved from STN Database accession No. 1965:51476, ISSN: 0044-460X," Zhurnal Obshchei Khimii, vol. 3.

Greene, T. W. et al., "Protective Groups in Organic Synthesis," Third Edition, pp. 494-653 (1999).

Hayashi S. et al., "Impairment by activation of TRPA1 of gastric epithelial restitution in a wound model using RGM1 cell monolayer," Infammopharmacology, 15(5):218-222 (2007).

Hill, Kerstin et al., "TRPA1 is Differentially Modulated by the Amphipathic Molecules Trinitrophenol and Chlorpomazine," The Journal of Biological Chemistry, 282(10):7145-7153 (2007).

Hinman A., et al., "TRP channel activation by reversible covalent modification," Proceedings of the National Academy of Science U.S.A., 103(51):19564-19568 (2006).

Jaquemar Daniel et al., "An Ankyrin-like Protein with Transmembrane Domains is Specifically Lost after Oncogenic Transformation of Human Fibroblasts," The Journal of Biological Chemistry, 274(11):7325-7333 (1999).

Jordt Sven-Eric et al., "Mustard oils and cannabinoids excite sensory nerve fibres through the TRP channel ANKTM1," Nature Publishing Group, 427:260-265 (2004).

Katsura, H. et al., "Activation of extracellular signal-regulated protein kinases 5 in primary afferent neurons contributes to heat and cold hyperalgesia after inflammation," Journal of Neurochemistry, 102(5):1614-1624 (2007).

Katsura, H. et al., "Antisense knock down of TRPA1, but not TRPM8, alleviates cold hyperalgesia after spinal nerve ligation in rats," Experimental Neurology, Elsevier Inc., 200:112-123 (2006).

Kimball, E. S. et al., "Stimulation of neuronal receptors, neuropeptides and cytokines during experimental oil of mustard colitis," Neurogastroenterology & Motility, 19:390-400 (2007).

Knowles P. Jonathan, et al., "The Heck Mizoroki cross-coupling reaction: a mechanistic perspective," Organic & Biomolecular Chemistry, 5:31-44 (2007).

Kochukov, M. Y., et al., "Thermosensitive TRP ion channels mediate cytosolic calcium response in human synoviocytes, XP002514988 ISSN: 0363-6143 1522-1563," American Journal of Physiology—Cell Physiology, 291(3):C424-C432 (2006).

Kulikova, D. A., et al., "Database CA (Online) Chemical Abstracts Service, Columbus, Ohio, US: Biologically active derivatives of thiophene. II. Synthesis and biological activity of some thiophene unsaturated ketones and their derivatives, XP002518709," (1980).

Kwan, Y. Kelvin et al., "TRPA1 Contributes to Cold, Mechanical, and Chemical Nociception but is not Essential for Hair-Cell Transduction," Neuron, Elsevier Inc., 50:277-289 (2006).

Lalezari, I. et al., "Selenium heterocycles. XXIV(1). 4-Substituted vinyl and 4-phenyl-1, 3-butadienyl-1, 2, 3-selenadiazol es and related compounds, XP002518706," Journal of Heterocycle Chemistry, 16(7):1405-1407 (1979).

Ley V., Steven, "Tetraproplyammonium Perruthenate, Pr 4N+ Ru4N, TPAP: A Catalytic Oxidant for Organic Synthesis," Review, pp. 639-666 (1994).

Lipton F. Michael, et al., "Conversion of Esters to Amides With Dimethylaluminum Amides: N, N-Dimethylcyclohexanecarboxamide," Organic Syntheses, vol. 6 and 59, pp. 492 and 49, 1979 and 1988.

(56) References Cited

OTHER PUBLICATIONS

MacPherson J. Lindsey, et al., The Pungency of Garlic: Activation of TRPA1 and TRPV1 in Response to Allicin, Current Biology, Elsevier Inc., 15:929-934 (2005).

MacPherson, L. J., et al., "Noxious compounds activate TRPA1 ion channels through covalent modification of cysteines," Nature, 445:541-545 (2007).

Mazik et al., Monatshefte fur Chemie, 127:1161-65, (1996).

McMahon S. B., et al., "Increasingly Irritable and close to tears: TRPA1 in inflammatory pain," Cell, 124 (6):1123-1125 (2005).

Montalbetti A. G. N. Christian et al., Amide bond formation and peptide coupling,: Tetrahedron, 61:10827-10852 (2005).

Nagata, Keiichi et al., Nociceptor and Hair Cell Transducer Properties of TRPA1, a Channel for Pain and Hearing, The Journal of Neuroscience, 25(16):4052-4061 (2005).

Niforatos, Wende et al., "Activation of TRPA1 Channels of the Fatty Acid Amide Hydrolase Inhibitor 3-Carbamoylbiphenyl-3yl cyclohexylcarbamate (URB597)," Molecular Pharmacology, 71(5):1209-1216 (2007).

Obata, Koichi et al., "TRPA1 induced in sensory neurons contributes to cold hyperalgesia after inflammation and nerve injury," The Journal of Clinical Investigation, 115(9):2393-2401 (2005).

Palacios et al., Tetrahedron, 54(3/4):599-614 (1998).

Pappalardo, Giovanni, "Database CA (Online) Chemical Abstracts Service, Columbus, Ohio, US: Ultraviolent absorption spectra of 5-substituted-2-nitrothiophenes and their vinyl analogs," XP002518711 retrieved from STN Database accession No. 1960:62656 abstract, (1959).

Patani et al., Chem Rev, 96:3147-3176 (1996).

Penuelas, A. et al., "Contractile effect of TRPA1 receptor agonists in the isolated mouse intestine," European Journal of Pharmacology, 576(1-3):143-150 (2007).

Petrus, Matt et al., "A role of TRPA1 in mechanical hyperalgesia is revealed by pharmacological inhibition," XP002514985, Molecular Pain, 3:40 (2007).

Prescott, et al., "Lipid Vesicles as Carriers for Introducing Biologically Active Materials into Cells," Methods in Cell Biology, Academic Press, 14:33-71 (1976).

Simon et al., "How irritating: the role of TRPA1 in sensing cigarette smoke and aerogenic oxidants in the airways," Journal of Clinical Investigation, 118:2383-2386 (2008).

TRPA1 ANTAGONISTS

This application is filed as a continuation application of U.S. patent application Ser. No. 12/348,065, filed Jan. 2, 2009, which claims priority to U.S. patent application Ser. No. 61/019,030, filed Jan. 4, 2007. The entire text of the aforementioned applications is incorporated herein by reference in its entirety.

TECHNICAL FIELD

The present invention generally relates to TRPA1 antagonists, compositions comprising such compounds, and methods of treating conditions and disorders using such compounds and compositions.

BACKGROUND

TRPA1 is a nonselective cation channel that belongs to the superfamily of Transient Receptor Potential (TRP) ion channels, like other family members, functional TRPA1 channels are formed by tetramerization of 4 subunits, each containing six transmembrane domains, a pore loop between transmembrane domain 5 (S5) and 6 (S6), and intracellular N- and C-termini. TRPA1 is expressed in sensory neurons and co-localized with pain markers such as TRPV1, calcitonin gene-related peptide and bradykinin receptor (Nagata, K. et al., Journal of Neuroscience 2005, 25, 4052-4061; Story, G. M. et al., Cell 2003, 112, 819-829; Corey, D. P. et al., Nature 2004, 432, 723-730; Bautista, D. M. et al., Proceedings of the National Academy of Science U.S.A. 2005, 102, 12248-12252; Jaquemar, D. et al., Journal of Biological Chemistry 1999, 274, 7325-7333). In pain models, knockdown of TRPA1 expression by gene specific antisenses prevented and reversed cold hyperalgesia induced by inflammation and nerve injury (Obata, K. et al., Journal of Clinical Investigation 2005, 115, 2393-2401; Jordt, S. E, et al., Nature 2004, 427, 260-265; Katsura, H. et al., Exploratory Neurology 2006, 200, 112-123). Furthermore, TRPA1 gene knockout resulted in impaired sensory functions and deficits in bradykinin-evoked pain hypersensitivity (Kwan, K. Y. et al. Neuron 2006, 50, 277-289; Bautista, D. M. et al. Cell 2006, 124, 1269-1282). Collectively, these data suggest that TRPA1 plays an important role in sensory functions and pain states. As a ligand-gated channel, TRPA1 can be activated by a variety of stimuli, including noxious cold, intracellular $Ca^{2+}$, endogenous substances (e.g., bradykinin), pungent natural products (e.g., allyl isothiocyanate, or AITC), environmental irritants (e.g., acrolein), amphipathic molecules (e.g., trinitrophenol and chlorpromazine) and pharmacological agents (e.g., URB597) (Macpherson, L. J. et. al., Current Biology 2005, 15, 929-934; Bandell, M. et al., Neuron 2004, 41, 849-857). Bradykinin activates TRPA1 indirectly through the phospholipase C pathway following binding of bradykinin to its receptors. Trinitrophenol and chlorpromazine open TRPA1 by inducing curvature or crenation in the lipid bilayer membrane (Xu, H. et al., Nat. Neurosci. 2006, 9, 628-635; Hill, K. and Schaefer, M., J. Biol. Chem. 2007, 282, 7145-7153; Niforatos, W. et. al., Molecular Pharmacology 2007, 71, 1209-1216). Most recently, it was shown that TRPA1 agonists could directly interact with the channel protein. AITC and cinnamaldehyde covalently modify several cysteine and lysine residues localized in the cytoplasmic N terminus and activate the channel (Hinman, A., Chuang, H. H., Bautista, D. M., and Julius, D. Proceedings of the National Academy of Science U.S.A, 2006, 103, 19564-19568; Macpherson, L. J., Dubin, A, E., Evans, M. J., Marr, F., Schultz, P. G., Cravatt, B. F., and Patapoutian, A., Nature 2007, 445, 541-545). In addition, intracellular $Ca^{2+}$ binds to the N-terminus EF-hand domains and mediates channel opening (Zurborg, S. et al., Nature Neuroscience 2007, 10, 277-279). Together these findings have revealed potential physiological roles of TRPA1, and also indicate that TRPA1 channel gating may involve different mechanisms and molecular determinants.

Thus, modulation of TRPA1 can have many industrial and therapeutic applications. For example, TRPA1 antagonists may fulfill the need in the art for new analgesic pharmaceuticals suitable for the treatment and/or prophylaxis of nociceptive and neuropathic pain in mammals, especially in humans.

SUMMARY

Disclosed herein are compounds of formula (I), or pharmaceutical salts, solvates, prodrugs, salts of prodrugs, or combinations thereof,

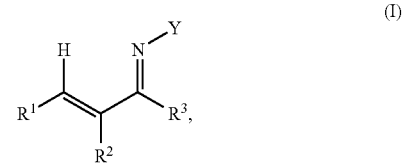

wherein $R^1$ is pyridin-3-yl, pyridin-4-yl, thien-2-yl, thien-3-yl, isoquinolin-4-yl, quinolin-3-yl, or quinolin-4-yl; each of which is optionally substituted with 1, 2, 3, 4, or 5 substituents as represented by $R^j$;

$R^j$, at each occurrence, is independently alkyl, alkenyl, alkynyl, —CN, halogen, —OR$^a$, —NO$_2$, —N(R$^a$)(R$^b$), —N(R$^b$)C(O)R$^a$, —N(R$^b$)S(O)$_2$R$^{1a}$, —N(R$^b$)C(O)OR$^a$, —N(R$^b$)C(O)N(R$^a$)(R$^b$), —N(R$^b$)S(O)$_2$N(R$^a$)(R$^b$), —C(O)R$^a$, —C(O)OR$^a$, —C(O)N(R$^a$)(R$^b$), —SR$^a$, —SF$_5$, —S(O)R$^{1a}$, —S(O)$_2$R$^{1a}$, —S(O)$_2$OR$^{1a}$, —S(O)$_2$N(R$^a$)(R$^b$), —(CR$^d$R$^e$)$_q$—CN, haloalkyl, —(CR$^d$R$^e$)$_q$—OR$^a$, —(CR$^d$R$^e$)$_q$—NO$_2$, —(CR$^d$R$^e$)$_q$—N(R$^a$)(R$^b$), —(CR$^d$R$^e$)$_q$—N(R$^b$)C(O)R$^a$, —(CR$^d$R$^e$)$_q$—N(R$^b$)S(O)$_2$R$^{1a}$, —(CR$^d$R$^e$)$_q$—N(R$^b$)C(O)OR$^a$, —(CR$^d$R$^e$)$_q$—N(R$^b$)C(O)N(R$^a$)(R$^b$), —(CR$^d$R$^e$)$_q$—N(R$^b$)S(O)$_2$N(R$^a$)(R$^b$), —(CR$^d$R$^e$)$_q$—C(O)R$^a$, —(CR$^d$R$^e$)$_q$—C(O)OR$^a$, —(CR$^d$R$^e$)$_q$—C(O)N(R$^a$)(R$^b$), —(CR$^d$R$^e$)$_q$—S(O)$_2$R$^{1a}$, —(CR$^d$R$^e$)$_q$—S(O)$_2$OR$^{1a}$, and —(CR$^d$R$^e$)$_q$—S(O)$_2$N(R$^a$)(R$^b$);

$R^2$ is hydrogen, $C_{1-6}$ alkyl, or haloalkyl;

$R^3$ is $C_{1-6}$ alkyl, haloalkyl, or cyclopropyl; wherein the cyclopropyl is optionally substituted with 1, 2, 3, 4, or 5 substituents independently selected from the groups consisting of alkyl, halogen, and haloalkyl;

Y is —OR$^f$, —N(R$^f$)(R$^g$), —N(R$^f$)C(O)R$^g$, —N(R$^f$)S(O)$_2$R$^g$, or —N(R$^f$)C(O)N(R$^f$)(R$^g$);

$R^{1a}$, at each occurrence, is independently alkyl or haloalkyl;

$R^a$ and $R^b$, at each occurrence, are each independently hydrogen, alkyl, or haloalkyl;

$R^d$ and $R^e$, at each occurrence, are each independently hydrogen, alkyl, halogen, or haloalkyl;

$R^f$ and $R^g$, at each occurrence, is independently hydrogen, alkyl, or haloalkyl; and q is 1, 2, 3, or 4;

with the proviso that the compound is not 1-(isoqinolin-4-yl)pent-1-en-3-one oxime;
1-(quinolin-4-yl)pent-1-en-3-one oxime;
1-(quinolin-3-yl)pent-1-en-3-one oxime;
(1E,3E)-4-methyl-1-(thien-2-yl)pent-1-en-3-one oxime;
(1E,3Z)-4-methyl-1-(thien-2-yl)pent-1-en-3-one oxime;
(1E,3E)-4,4-dimethyl-1-(thien-2-yl)pent-1-en-3-one oxime;
(1E,3Z)-4,4-dimethyl-1-(thien-2-yl)pent-1-en-3-one oxime;
(1E)-1-(thien-2-yl)pent-1-en-3-one oxime;
(1Z)-1-(thien-2-yl)pent-1-en-3-one oxime;
(3E)-1-(thien-2-yl)pent-1-en-3-one oxime;
(3Z)-1-(thien-2-yl)pent-1-en-3-one oxime;
4-(pyridin-3-yl)but-3-en-2-one oxime;
4-(pyridin-4-yl)but-3-en-2-one oxime;
4-(5-chloropyridin-3-yl)but-3-en-2-one oxime;
4-(3-chloropyridin-4-yl)but-3-en-2-one oxime;
3-methyl-4-(pyridin-3-yl)but-3-en-2-one oxime;
3-methyl-4-(pyridin-4-yl)but-3-en-2-one oxime;
3-methyl-4-(5-chloropyridin-3-yl)but-3-en-2-one oxime;
3-methyl-4-(3-chloropyridin-4-yl)but-3-en-2-one oxime;
1-(pyridin-3-yl)pent-1-en-3-one oxime;
1-(pyridin-4-yl)pent-1-en-3-one oxime;
1-(5-chloropyridin-3-yl)pent-1-en-3-one oxime; or
1-(3-chloropyridin-4-yl)pent-1-en-3-one oxime.

Further, disclosed herein are methods are treating disorders that are ameliorated by inhibition of TRPA1. Such methods comprise of administering to the subject therapeutically effective amount(s) of one or more TRPA1 antagonists, alone, or in combination with one or more pharmaceutically acceptable carriers. The TRPA1 antagonists employed are selected from compounds of formula (I), or solvates, pharmaceutical salts, prodrugs, salts of prodrugs, or my combinations thereof,

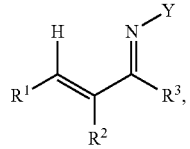

(I)

wherein $R^1$ is pyridin-3-yl, pyridin-4-yl, thien-2-yl, thien-3-yl, isoquinolin-4-yl, quinolin-3-yl, or quinolin-4-yl; each of which is optionally substituted with 1, 2, 3, 4, or 5 substituents as represented by $R^j$;

$R^j$, at each occurrence, is independently alkyl, alkenyl, alkynyl, —CN, halogen, —$OR^a$, —$NO_2$, —$N(R^a)(R^b)$, —$N(R^b)C(O)R^a$, —$N(R^b)S(O)_2R^{1a}$, —$N(R^b)C(O)OR^a$, —$N(R^b)C(O)N(R^a)(R^b)$, —$N(R^b)S(O)_2N(R^a)(R^b)$, —$C(O)R^a$, —$C(O)OR^a$, —$C(O)N(R^a)(R^b)$, —$SR^a$, —$SF_5$, —$S(O)R^{1a}$, —$S(O)_2R^{1a}$, —$S(O)_2OR^{1a}$, —$S(O)_2N(R^a)(R^b)$, —$(CR^dR^e)_q$—CN, haloalkyl, —$(CR^dR^e)_q$—$OR^a$, —$(CR^dR^e)_q$—$NO_2$, —$(CR^dR^e)_q$—$N(R^a)(R^b)$, —$(CR^dR^e)_q$—$N(R^b)C(O)R^a$, —$(CR^dR^e)_q$—$N(R^b)S(O)_2R^{1a}$, —$(CR^dR^e)_q$—$N(R^b)C(O)OR^a$, —$(CR^dR^e)_q$—$N(R^b)C(O)N(R^a)(R^b)$, —$(CR^dR^e)_q$—$N(R^b)S(O)_2N(R^a)(R^b)$, —$(CR^dR^e)_q$—$C(O)R^a$, —$(CR^dR^e)_q$—$C(O)OR^a$, —$(CR^dR^e)_q$—$C(O)N(R^a)(R^b)$, —$(CR^dR^e)_q$—$S(O)_2R^{1a}$, —$(CR^dR^e)_q$—$S(O)_2OR^{1a}$, and —$(CR^dR^e)_q$—$S(O)_2N(R^a)(R^b)$;

$R^2$ is hydrogen, $C_{1-6}$ alkyl, or haloalkyl;

$R^3$ is $C_{1-6}$ alkyl, haloalkyl, or cyclopropyl; wherein the cyclopropyl is optionally substituted with 1, 2, 3, 4, or 5 substituents independently selected from the groups consisting of alkyl, halogen, and haloalkyl;

Y is —$OR^f$, —$N(R^f)(R^g)$, —$N(R^f)C(O)R^g$, —$N(R^f)S(O)_2R^g$, or —$N(R^f)C(O)N(R^f)(R^g)$;

$R^{1a}$, at each occurrence, is independently alkyl or haloalkyl;

$R^a$ and $R^b$, at each occurrence, are each independently hydrogen, alkyl, or haloalkyl;

$R^d$ and $R^e$, at each occurrence, are each independently hydrogen, alkyl, halogen, or haloalkyl;

$R^f$ and $R^g$, at each occurrence, is independently hydrogen, alkyl, or haloalkyl; and q is 1, 2, 3, or 4;

Some method are directed to treating disorders or conditions such as, but not limited to, the following: acute cerebral ischemia, chronic pain, neuropathic pain, inflammatory pain, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, menstrual pain; bladder disease such as incontinence, micturition disorder, renal colic, and cystitis; inflammation such as burns, rheumatoid arthritis and osteoarthritis; neurodegenerative disease such as stroke, post stroke pain and multiple sclerosis; pulmonary disease such as asthma, cough, chronic obstructive pulmonary disease (COPD) and broncho constriction; gastrointestinal disease such as gastroesophageal reflux disease (GERD), dysphagia, ulcer, irritable bowel syndrome (IBS), inflammatory bowel disease (IBD), colitis and Crohn's disease; ischemia such as cerebrovascular ischemia; emesis is such as cancer chemotherapy-induced emesis, or obesity, said method comprising the step of administering therapeutically effective amounts of one or more compounds of formula (I), or solvates, of pharmaceutically acceptable salts thereof, to a subject in need thereof, with or without one or more pharmaceutically acceptable carriers. In some methods, the subject being treated is human. Some methods further comprising co-administering with one or more second pain reducing agents.

Another aspect of the present invention is directed to pharmaceutical compositions comprising one or more compounds of formula (I), or solvates or pharmaceutically acceptable salts thereof, and one or more pharmaceutically acceptable carriers. Some pharmaceutical compositions may further comprise one or more second pain reducing agents.

The invention further provides a use of one or more compounds of formula (I), or solvates or pharmaceutically acceptable salts thereof, in the manufacture of a medicament for the treatment of conditions and disorders disclosed herein, alone or is combination with one or more second pain reducing agent.

For example, the second pain reducing agent can be an analgesic agent selected from acetaminophen, or a nonsteroidal anti-inflammatory drug (NSAID), or combinations thereof. In some embodiments, the nonsteroidal anti-inflammatory drug is ibuprofen. The second pain reducing agent can also be opioids.

DETAILED DESCRIPTION

Compounds of formula (I) are disclosed in this invention,

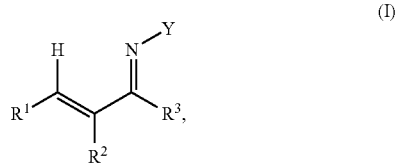

(I)

wherein $R^1$, $R^2$, $R^3$, and Y are defined above in the Summary and below in the Detailed Description. Preferably, compounds of the invention are TRPA1 antagonists. Further, compositions comprising such compounds and methods for treating conditions and disorders using such compounds and compositions are also disclosed.

Compounds disclosed herein may contain one or more variable(s) that occur more than one time in any substituent or in the formulae herein. Definition of a variable on each occurrence is independent of its definition at another occurrence. Further, combinations of substituents are permissible only if such combinations result in stable compounds. Stable compounds are compounds, which can be isolated from a reaction mixture.

a. Definition

As used in the specification and the appended claims, unless specified to the contrary, the following terms have the meaning indicated:

The term, "alkenyl" as used herein, means a straight or branched chain hydrocarbon containing from 2 to 10 carbons and containing at least one carbon-carbon double bond. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkyl" as used herein, means a straight or branched saturated hydrocarbon chain containing from 1 to 10 carbon atoms. The term "$C_{1-6}$ alkyl" means a straight or branched saturated hydrocarbon chain containing from 1 to 6 carbon atoms. The term "$C_{1-4}$ alkyl" means a straight or branched saturated hydrocarbon chain containing from 1 to 4 carbon atoms. Representative examples of alkyl include, but are not limited to, methyl, ethyl, n-propyl iso-propyl, n-butyl, sec-butyl, iso-butyl, tert-butyl, n-pentyl, isopentyl, neopentyl, n-hexyl, 3-methylhexyl, 2,2-dimethylpentyl 2,3-dimethylpentyl, n-heptyl, n-octyl n-nonyl, and n-decyl.

The term "alkynyl" as used herein, means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "halo" or "halogen" as used herein, means —Cl, —Br, —I or —F.

The term "haloalkyl" as used herein, means at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 4,4,4-trifluorobutyl, and 2-chloro-3-fluoropentyl.

The term "subject" includes mammals, especially humans, as well as other non-human animals, e.g. horses, dogs, cats, and fish.

b. Compounds

Compounds of the invention have the general formula (I) as described above.

Particular values of variable groups in compounds of formula (I) are as follows. Such values may be used where appropriate with any of the other values, definitions, claims or embodiments defined hereinbefore or hereinafter.

In compounds of formula (I), $R^1$ has values as described in the Summary. In certain embodiments, $R^1$ is pyridin-3-yl or pyridin-4-yl. Some embodiments are directed to compounds wherein $R^1$ is thien-2-yl or thien-3-yl. Yet other embodiments are directed to compounds wherein $R^1$ is isoquinolin-4-yl, quinolin-3-yl, or quinolin-4-yl. Each of the rings as represented by $R^1$ is independently unsubstituted or substituted as described in the Summary. Certain embodiments are directed to compounds wherein the optional substituents ($R^j$) of $R^1$ is halogen (for example, but not limited thereto, F), alkyl (for example, but not limited thereto, methyl), haloalkyl (for example, but not limited thereto, trifluoromethyl), or —$OR^a$ wherein $R^a$ is as described in the Summary. For example, $R^a$ is alkyl such as, but not limited to, methyl.

$R^2$ is hydrogen, $C_{1-6}$ alkyl, or haloalkyl. For example, $R^2$ is $C_{1-6}$ alkyl such as, but not limited to, methyl. In some embodiments, $R^2$ is hydrogen.

$R^3$ is $C_{1-6}$ alkyl, haloalkyl, or optionally substituted cyclopropyl. For example, $R^3$ is $C_{1-6}$ alkyl such as, but not limited to, methyl, ethyl, n-propyl, tert-butyl, n-butyl, and isopropyl. In certain embodiments, $R^3$ is ethyl.

Y is —$OR^f$, —$N(R^f)(R^g)$, —$N(R^f)C(O)R^g$, —$N(R^f)S(O)_2R^g$, or —$N(R^f)C(O)N(R^f)(R^g)$; wherein $R^f$ and $R^g$ are as described in the Summary. In certain embodiments Y is —OH or —$O(C_{1-4}$ alkyl), for example, Y is —OH or —O(methyl). Certain embodiments are directed to compounds wherein Y is —$N(R^f)(R^g)$, —$N(R^f)C(O)R^g$, —$N(R^f)S(O)_2R^g$, or —$N(R^f)C(O)N(R^f)(R^g)$; and $R^f$ and $R^g$ are as described in the Summary. $R^f$ and $R^g$, for example, are each independently hydrogen or $C_{1-4}$ alkyl. (e.g. methyl). In certain embodiments, Y is —OH. In other embodiments, Y is —$O(C_{1-4}$ alkyl), for example, Y is —O(methyl).

It is appreciated that the present invention contemplates compounds of Formula (I), pharmaceutically acceptable salts, prodrugs, salts of prodrugs, solvates, or any combinations thereof with combinations of the above embodiments, including particular, more particular and preferred embodiments.

Accordingly, examples of a group of compounds of Formula (I) include, but are not limited to, those wherein $R^2$ is $C_{1-6}$ alkyl and $R^3$ is $C_{1-6}$ alkyl. For example, $R^2$ is methyl, $R^3$, for example, is methyl, ethyl, n-propyl, tert-butyl, n-butyl, or isopropyl. In certain embodiments, $R^3$ is ethyl.

Other examples of a group of compounds of Formula (I) include, but are not limited to, those wherein $R^2$ is hydrogen and $R^3$ is $C_{1-6}$ alkyl. $R^3$, for example, is methyl, ethyl, n-propyl, tert-butyl, n-butyl, and isopropyl. In certain embodiments, $R^3$ is ethyl.

Yet other examples of a group of compounds of formula (I) include, but are not limited to, those wherein Y is —$OR^f$, $R^2$ is alkyl, $R^3$ is $C_{1-6}$ alkyl, and $R^f$ is as described in the Summary. For example, $R^2$ is methyl. $R^3$ for example, is methyl, ethyl, n-propyl, tert-butyl, n-butyl, or isopropyl. In certain embodiments, $R^3$ is ethyl. $R^f$, for example, is hydrogen or $C_{1-4}$ alkyl.

Other examples of a group of compounds of formula (I) include, but are not limited to, those wherein Y is —$OR^f$, $R^2$ is hydrogen, $R^3$ is $C_{1-6}$ alkyl, and $R^f$ is m described in the Summary. $R^3$ for example, is methyl, ethyl, n-propyl, tert-butyl, n-butyl, or isopropyl. In certain embodiments, $R^3$ is ethyl, $R^f$, for example, is hydrogen or $C_{1-4}$ alkyl.

Yet other examples of a group of compounds of formula (I) include, but are not limited to, those wherein Y is —OH, $R^2$ is $C_{1-6}$ alkyl and $R^3$ is $C_{1-6}$ alkyl. For example, $R^2$ is methyl. $R^3$ for example, is methyl, ethyl, n-propyl tert-butyl, n-butyl, or isopropyl. In certain embodiments, $R^3$ is ethyl.

Other examples of a group of compounds of formula (I) include, but are not limited to, those wherein Y is —O($C_{1-4}$ alkyl), $R^2$ is $C_{1-6}$ alkyl, and $R^3$ is $C_{1-6}$ alkyl. For example, $R^2$ is methyl. $R^3$, for example, is methyl, ethyl, n-propyl, tert-butyl, n-butyl or isopropyl. In certain embodiments, $R^3$ is ethyl. Y, for example, is —O(methyl).

Yet other examples of a group of compounds of formula (I) include, but are not limited to, those wherein Y is —N($R^f$)($R^g$), —N($R^f$)C(O)$R^g$, —N($R^f$)S(O)$_2R^g$, or —N($R^f$)C(O)N($R^f$)($R^g$); $R^2$ is $C_{1-6}$ alkyl, $R^3$ is $C_{1-6}$ alkyl, and $R^f$ and $R_g$ are as described in the Summary and the Detailed Description sections. For example, $R^2$ is methyl. $R^3$, for example, is methyl, ethyl, n-propyl, tert-butyl, n-butyl, or isopropyl. In certain embodiments, $R^3$ is ethyl.

Further examples of a group of compounds of formula (I) include, but are not limited to, those wherein Y is —OH, $R^2$ is hydrogen, and $R^3$ is $C_{1-6}$ alkyl. $R^3$, for example, is methyl, ethyl, n-propyl, tert-butyl, n-butyl or isopropyl in certain embodiments, $R^3$ is ethyl.

Other examples of a group of compounds of formula (I) include, but are not limited to, those wherein Y is —O($C_{1-4}$ alkyl), $R^2$ is hydrogen, and $R^3$ is $C_{1-6}$ alkyl. $R^3$, for example, is methyl, ethyl n-propyl, tert-butyl, n-butyl, or isopropyl. In certain embodiments, $R^3$ is ethyl. Y, for example, is —O(methyl).

Yet other examples of a group of compounds of formula (I) include, but are not limited to, those wherein Y is —N($R^f$)($R^g$), —N($R^f$)C(O)$R^g$, —N($R^f$)S(O)$_2R^g$, or —N($R^f$)C(O)N($R^f$)($R^g$); $R^2$ is hydrogen, $R^3$ is $C_{1-6}$ alkyl, and $R^f$ and $R_g$ are as described in the Summary and the Detailed Description sections, $R^3$, for example, is methyl, ethyl, n-propyl, tert-butyl n-butyl, or isopropyl. In certain embodiments, $R^3$ is ethyl.

Within, the groups of compounds of formula (I) as described herein above, $R^1$ has values as described in the Summary and the Detailed Description. Thus, examples of a subgroup of compounds of formula (I) include those wherein $R^1$ is pyridin-3-yl or pyridin-4-yl, each of which is optionally substituted as described in the Summary and the Detailed Description.

Other examples of a subgroup include, but am not limited to, those wherein $R^1$ is thien-2-yl or thien-3-yl, each of which is optionally substituted as described in the Summary and the Detailed Description.

Yet other examples of a subgroup include, but are not limited to, those wherein $R^1$ is isoquinolin-4-yl, quinolin-3-yl, or quinolin-4-yl; each of which is optionally substituted as described in the Summary and the Detailed Description.

Compounds of formula (I) may contain one or more asymmetrically substituted atoms. The present invention contemplates various individual stereoisomers (including enantiomers and diastereomers) and mixtures thereof. Individual stereoisomers of compounds of the present invention, may be prepared synthetically from commercially available starting materials that contain asymmetric or chiral centers or by preparation of racemic mixtures followed by resolution of the individual stereoisomer using methods that are known to those of ordinary skill in the art. Examples of resolution are, for example, (i) attachment of a mixture of enantiomers to a chiral auxiliary, separation of the resulting mixture of diastereomers by recrystallization or chromatography, followed by liberation of the optically pure product; or (ii) separation of the mixture of enantiomers or diastereomers on chiral chromatographic columns.

The invention also contemplates the various geometric isomers and mixtures thereof resulting from the disposition of substituents around a carbon-carbon double bond, a carbon-nitrogen double bond, a cycloalkyl group, or a heterocycle group. Substituents around a carbon-carbon double bond or a carbon-nitrogen double bond are designated as being of Z or E configuration and substituents around a cycloalkyl or heterocycle are designated as being of cis or trans configuration.

Examples of some of the possible geometrical isomers of compounds of formula (I) include, but are not limited to, (Ia), (Ib), (Ic), and (Id).

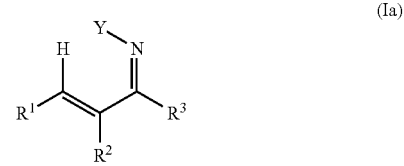

(Ia)

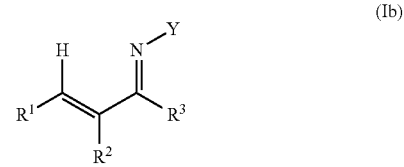

(Ib)

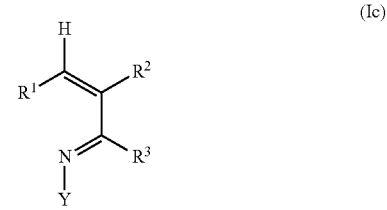

(Ic)

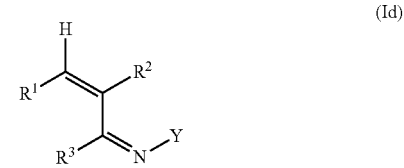

(Id)

wherein $R^1$, $R^2$, $R^3$, and Y have meanings as defined in the Summary and the Detailed Description. It is understood that embodiments for $R^1$, $R^2$, $R^3$, and Y, and combinations of embodiments, including particular, and more particular embodiments as described for formula (I), are also contemplated for compounds of formula, (Ia), (Ib), (Ic), and (Id).

Within the present invention it is to be understood that compounds disclosed herein may exhibit the phenomenon of tautomerism and all tautomeric isomers are included in the scope of the invention.

Thus, the formulae drawings within this specification can represent only one of the possible tautomeric, geometric, or stereoisomeric forms. It is to be understood that the invention encompasses any tautomeric, geometric, or stereoisomers form, and mixtures thereof, and is not to be limited merely to any one tautomeric, geometric, or stereoisomeric form utilized within the formulae drawings.

Exemplary compounds of formula (I) include, but are not limited to:

(1E,3E)-1-(6-fluoropyridin-3-yl)-2-methylpent-1-en-3-one oxime;
(1E,3E)-2-methyl-1-thien-2-ylpent-1-en-3-one oxime;
(1E,3E)-1-(6-methoxypyridin-3-yl)-2-methylpent-1-en-3-one oxime;
(1E,3E)-2-methyl-1-thien-3-ylpent-1-en-3-one oxime;
(1E,3E)-2-methyl-1-pyridin-3-ylpent-1-en-3-one oxime; and
(1E,3E)-2-methyl-1-pyridin-4-ylpent-1-en-3-one oxime;
The following compounds are also contemplated:
(1E,3E)-2-methyl-1-(6-methylpyridin-3-yl)pent-1-en-3-one oxime;
(1E,3E)-2-methyl-1-quinolin-3-ylpent-1-en-3 oxime;
(1E,3E)-2-methyl-1-(4-methylpyridin-3-yl)pent-1-en-3-one oxime;
(1E,3E)-2-methyl-1[6-(trifluoromethyl)pyridin-3-yl]pent-1-en-3-one oxime;
(1E,3E)-1-(isoquinolin-4-yl)-2-methylpent-1-en-3-one oxime;
(1E,3E)-2-methyl-1-pyridin-4-ylhex-1-en-3-one oxime;
(2E,3Z)-4-pyridin-4-yl-3-(trifluoromethyl)but-3-en-2-one oxime;
(2E,3E)-1-pyridin-4-yl-2-(trifluoromethyl)pent-1-en-3-one oxime;
(2E,3E)-3-methyl-4-pyridin-4-ylbut-3-en-2-one O-methyloxime;
(1E,3E)-2-methyl-1-pyridin-4-ylpent-1-en-3-one O-methyloxime;
(1E,3Z)-2-methyl-1-pyridin-4-ylpent-1-en-3-one oxime; and
(1E,3Z)-2-methyl-1-(2-methylpyridin-4-yl)pent-1-en-3-one oxime.

c. Biological Data
(i) In Vitro Data—Determination of Inhibition Potencies

Molecular biology and transient expression were performed as described in Chen, J. et al., Journal of Biomolecular Screening 2007, 12, 61-69. Briefly, TRPA1 full length cDNA was amplified from human dorsal root ganglia total RNA (BD Bioscience Clontech, Palo Alto, Calif., USA) and was cloned into pcDNA3.1/V5-His Topo vector (Invitrogen, Carlsbad, Calif.). Large scale transient transfection was performed using the FreeStyle™ 293 Expression System as recommended by the manufacturer (Invitrogen). HEK293-F cells were grown in suspension in flasks (cell volume 30 ml, to 1 liter) or in a Wave Bioreactor (Wave Biotech, Somerset, N.J. (6 liters). To support high density, suspension culture and transfection, cells were cultured in Free Style 293 media, an optimized, serum free formulation. 293fectin™ (Invitrogen) was used as transfection reagent. In a transfection of $3\times10^7$ cells (30 mL volume), 30 μg of plasmid DNA and 40 μL 293 fectin were used. For a larger volume transfection, each reagent was scaled up proportionally. Two days post-transfection, cells were harvested by centrifugation (1000×g, 5 minutes) and resuspended to a density of $1.5\times10^7$ cells/mL in freezing medium (Freestyle media/10% serum/10% DMSO). Cells were transferred into cryovials in 2 mL aliquots, and these vials were placed in Nalgene Mr. Frosty slow-freeze devices (Sigma-Aldrich, St. Louis, Mo.) at −80° C. As needed, vials were removed from −80° C. and quickly thawed in a 37° C. water bath. Cells were aseptically transferred into conical tubes containing Freestyle media (10 mL/vial). After centrifugation at 1,000×g for 3-5 minutes, medium was removed by aspiration, and cells were resuspended in Freestyle medium at desired densities (typically $1\times10^6$ cells/mL). Re-suspended cells were seeded into black-walled clear-bottom 96-well Biocoat™ poly-D-lysine assay plated (BD Biosciences, Bedford, Mass.) ($10^5$ cells/well) and incubated overnight at 37° C. under a humidified 5% $CO_2$ atmosphere.

FLIPR Based Intracellular $Ca^{2+}$ Assay and Membrane Potential Assay $Ca^{2+}$ influx was measured using a FLIPR calcium assay kit (R8033; Molecular Devices, Sunnyvale, Calif.). The $Ca^{2+}$ indicator dye was dissolved in Hanks' balanced salt solution supplemented with 20 mM HEPES buffer (HBSS/HEPES) according to the manufacturer instructions. Prior to start of the assay, the medium was removed by aspiration, and cells were loaded with 100 μL $Ca^{2+}$ dye for 2 to 3 hours at room temperature. AITC (allyl isothiocyanate) was used to activate and open the channels. (4×) solutions of the test compounds were prepared in HBSS/HEPES, and 50 μL were added to the cells at a delivery rate of 10 μL/sec. Changes in fluorescence were measured over time in a fluorometric imaging plate reader (FLIPR), Molecular Devices). Two additions were made over the course of an experimental run. For agonist experiments, assay buffer was added at the 10 s time point, followed by addition of agonist at the 3 minute 10 sec time point. For antagonist experiments, the antagonist was added at the 10 sec time point, followed by addition of the agonist 3 minutes later. Final assay volume for both the agonist and antagonist experiments was 200 μL. Total length of an experimental run was 6.5 minutes.

Data was analyzed with GraphPad Prism® software (GraphPad Software, San Diego, Calif.), using a four-parameter logistic Hill equation to curve-fit concentration-effect data and derive $EC_{50}$ or $IC_{50}$ values. Numerical values are reported as mean±SEM (n=number of experiments). SEM is calculated by dividing the standard deviation by the square root of the sample size (minus 1).

Changes in membrane potential were measured in hTRPA1-expressing LSTT cells using a FLIJPR membrane potential assay kit (R8034, Molecular Devices). The procedure for thawing and plating the LSTT cells was identical to the $Ca^{2+}$ influx assay (see above). The membrane potential dye was dissolved in HBSS/HEPES buffer according to the manufacturer's instructions, and then cells were loaded with dye (100 μL/well) for 45 minutes to 2 hours at room temperature. The protocol for addition of chemical agents, and measurement of changes in fluorescence, was the same as the $Ca^{2+}$ influx assay, except for the emission filter setting. The results are shown in Table 1.

TABLE 1

| Example | Human TRPA1 $IC_{50}$ (μM) |
|---|---|
| 1 | 1.25 |
| 2 | 11 |
| 3 | 23.4 |
| 4 | 1.32 |
| 5 | 17 |
| 6 | 8.61 |
| 7 | >100 |
| 8 | >100 |
| 9 | >100 |
| 10 | >100 |
| 11 | >100 |

Certain compounds of formula (I) were tested in the assay described above and are effective TRPA1 antagonists with $IC_{50}$ values from about 100 μM to about 1 μM, for example, from about 25 μM to about 2 μM.

d. Methods of Using the Compounds

Compounds described, herein are TRPA1 antagonist and are capable of interfering with the expression, modification, regulation, or activation of TRPA1, or down-regulates one or more of the normal biological activities of TRPA1 (e.g. its ion-channel).

One embodiment of the present invention provides a method for treating a disorder that may be ameliorated by inhibiting TRPA1 receptor in a subject in need of such treatment. The method comprises administering a therapeutically effective amount of one or more compounds of formula (I), solvates, pharmaceutically acceptable salts, prodrugs, salts of prodrugs, or any combination thereof, alone or in combination with one or more pharmaceutically acceptable carriers.

Another embodiment of the present invention provides a method for treating pain (e.g. nociceptive pain, neuropathic pain, inflammatory pain, osteoarthritic pain, etc,) in a subject in need of such treatment. This method comprises administering a therapeutically effective amount of one or more compounds of formula (I), solvates, pharmaceutically acceptable salts, prodrugs, salts of prodrugs, or any combination thereof, alone or in combination with one or more pharmaceutically acceptable carriers.

Yet another embodiment of the present invention provides a method for prophylaxis or treatment of ischemia including acute cerebral ischemia, pain including chronic pain, neuropathic pain, nociceptive pain, allodynia, inflammatory pain, inflammatory hyperalgesia, post herpetic neuralgia, neuropathies, neuralgia, diabetic neuropathy, HIV-related neuropathy, nerve injury, rheumatoid arthritic pain, osteoarthritic pain, burns, back pain, visceral pain, cancer pain, dental pain, headache, migraine, carpal tunnel syndrome, fibromyalgia, neuritis, sciatica, pelvic hypersensitivity, pelvic pain, and menstrual pain; bladder disease such as incontinence and bladder overactivity, bladder cystitis, micturition disorder, and renal colic; inflammation such as burns, oral mucositis, rheumatoid arthritis and osteoarthritis; neurodegenerative disease such as stroke, post stroke pain and multiple sclerosis; pulmonary disease such as asthma, cough, chronic obstructive pulmonary disease (COPD) and bronchoconstriction; skin disorders such as psoriasis, eczema, and dermatitis; gastrointestinal disease such as gastroesophageal reflux disease (GERD), dysphagia, ulcer, irritable bowel syndrome (IBS), inflammatory bowel disease (IBD), colitis and Crohn's disease; ischemia such as cerebrovascular ischemia; emesis such as cancer chemotherapy-induced emesis, in mammals, especially humans. For example, the compounds of formula (I) are useful for the treatment of pain, particularly nociceptive and inflammatory pain, more particularly, osteoarthritic pain. This method comprises the step of administering to a subject in need thereof a therapeutically effective amount of one or more compounds of formula (I), solvates, pharmaceutically acceptable salts, prodrugs, salts of prodrugs, or any combination thereof alone or in combination with one or more pharmaceutically acceptable carriers.

Compounds of formula (I), including but not limited to those specified in the examples, solvates, pharmaceutically acceptable salts, prodrugs, salts of prodrugs, or any combination thereof, can be used for the prophylaxis or treatment of inflammatory, nociceptive, and neuropathic pain as demonstrated by Bautista, D. Cell 2006, 124, 1269-1282; Trevisani, M. et al. Proceedings of the National Academy of Sciences USA 2007, 104, 13519-13524; Dai, Y, et al. Journal of Clinical Investigation 2007, 117, 1979-1987; Diogenes, A. et al. Journal of Dental Research 2007, 86, 550-555; Katsura, H. et al. Journal of Neurochemistry 2007, 102, 1614-1624; and McMahon, S. B. et al. Cell 2006, 124, 1123-1125.

Compounds of formula (I), including but not limited to those specified in the examples, solvates, pharmaceutically acceptable salts, prodrugs, salts of prodrugs, or any combination thereof, can be used for the prophylaxis or treatment of colitis and Crohn's disease as demonstrated by Kimball E. S. et al. Neurogastroenterology & Motility 2007, 19, 90-400.

Compounds of formula (I), including but not limited to those specified in the examples, solvates, pharmaceutically acceptable salts, prodrugs, salts of prodrugs, or any combination thereof, can be used for the prophylaxis or treatment of respiratory hypersensitivity such as cough, asthma, and chronic obstructive pulmonary disease (COPD) as demonstrated by Andre et al., Journal of Clinical Investigation 2008, 118, 2374-2582; Bessac et al., Journal of Clinical Investigation 2008, 118, 1899-1910; and Simon and Liedtke, Journal of Clinical Investigation 2008, 118, 2383-2386.

Compounds of formula (I), including but not limited to those specified in the examples, solvates, pharmaceutically acceptable salts, prodrugs, salts of prodrugs, or any combination thereof, can be used for the prophylaxis or treatment of gastrointestinal diseases such as irritable bowel syndrome (IBS) and inflammatory bowel disease (IBD) as demonstrated by Penuelas, A. et al. European Journal of Pharmacology 2007, 576, 143-150 and Hayashi, S. et al. Inflammopharmacology 2007, 15, 218-222.

Compounds of formula (I), including but not limited to those specified in the examples, solvates, pharmaceutically acceptable salts, prodrugs, salts of prodrugs, or any combination thereof, can be used for the prophylaxis or treatment of cold hyperalgesia or cold sensitivity as demonstrated by Story, G. M. Current Neuropharmacology 2006, 4, 183-196 and Story, G. M. and Gereau, R. W. Neuron 2006, 50, 177-180.

Compounds of formula (I), including but not limited to those specified in the examples, solvates, pharmaceutically acceptable salts, prodrugs, salts of prodrugs, or any combination thereof, can be used as depilatory agents to prevent or reverse hirsutism as demonstrated by Kwan, K. Y. et al. Neuron 2006, 50, 277-289.

Compounds described herein may be administered alone, or in combination (i.e. co-administered) with one or more additional pharmaceutical agents such as a second pain reducing agent. For example, the second pain reducing agent can be an analgesic agent such as, but not limited to, acetaminophen, or a nonsteroidal anti-inflammatory drug (NSAID), or combination thereof. Examples of nonsteroidal anti-inflammatory drug (NSAID) include, but not limited to, aspirin, diclofenac, diflusinal etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin and zomepirac. Yet other class of second pain-reducing agent includes opioids. Other analgesic such as local anesthetics including anticonvulsants and antidepressant may also be used in the combination therapy. Administering one or more classes of drugs in addition to TRPA1 antagonists can provide more effective amelioration of pain. Combination therapy includes administration, of a single pharmaceutical dosage formulation containing one or more of the compounds of formula (I) and one or more additional pharmaceutical agents; as well as administration of the compounds of formula (I) and each additional pharmaceutical agent, in its own separate pharmaceutical dosage formulation. For example, one or more compounds of formula (I) and one or more additional pharmaceutical agents, may be administered to the patient together, in a single oral dosage composition having a fixed ratio of each active ingredient, such as a tablet or capsule; or each agent may be administered in separate oral dosage formulations.

Where separate dosage formulations are used, each active ingredient may be administered at essentially the same time (e.g., concurrently) or at separately staggered times (e.g., sequentially).

Actual dosage levels of active ingredients in the pharmaceutical compositions of this invention can be varied so as to obtain an amount of the active compound(s) that is effective to achieve the desired therapeutic response for a particular patient, compositions and mode of administration. The selected dosage level will depend upon the activity of the particular compound, the route of administration, the severity of the condition being treated and the condition and prior medical history of the patient being treated. However, it is within the skill of the art to start doses of the compound at levels lower than required to achieve the desired therapeutic effect and to gradually increase the dosage until the desired effect is achieved.

TRPA1 antagonists described herein can be administered alone, or as a pharmaceutical composition comprising a therapeutically effective amount of one or more of the TRPA1 antagonists in combination with one or more pharmaceutically acceptable carriers, with or without one or more second pain reducing agent. The phrase "therapeutically effective amount" means a sufficient amount of TRPA1 antagonist to treat disorders, at a reasonable benefit/risk ratio applicable to any medical treatment. It will be understood, however, that the total daily usage of the compounds and compositions of the invention will be decided by the attending physician within the scope of sound medical judgment. The specific therapeutically effective dose level for any particular patient will depend upon a variety of factors including the disorder being treated and the severity of the disorder; activity of the specific compound employed; fee specific composition employed; the age, body weight, general health, sex and diet of the patient; the time of administration, route of administration, and rate of excretion of the specific compound employed; the duration of the treatment; drugs used in combination or coincidental with the specific compound employed; and like factors well-known in the medical arts. For example, it is well within the skill of the art to start doses of the compound at levels lower than required to achieve the desired therapeutic effect and to gradually increase the dosage until the desired effect is achieved.

The total daily dose of the compounds of formula (I) administered to a human or lower animal range from about 0.10 μg/kg body weight to about 50 mg/kg body weight. More preferable doses can be in the range of from about 0.10 μg/kg body weight to about 10 mg/kg body weight. If desired, the effective daily dose can be divided into multiple doses for purposes of administration. Consequently, single dose compositions may contain such amounts or submultiples thereof to make up the daily dose.

e. Pharmaceutical Compositions

The present invention further provides pharmaceutical compositions that comprise TRPA1 antagonists of the present invention thereof. The pharmaceutical compositions comprise one or more compounds of formula (I), solvates, pharmaceutically acceptable salts, prodrugs, salts of prodrugs, of combinations thereof that may be formulated together with one or more pharmaceutically acceptable carriers.

Another aspect of the present invention provides a pharmaceutical composition comprising one or more compounds of formula (I), solvates, pharmaceutically acceptable salts, prodrugs, salts of prodrugs, or combinations thereof, and one or more pharmaceutically acceptable carriers, in combination with one or more second pain reducing agents. In certain embodiments, the second pain reducing agent is an analgesic such as acetaminophen, a nonsteroidal anti-inflammatory drug (NSAID), or combination thereof. In certain embodiments, the nonsteroidal anti-inflammatory drug is ibuprofen. In other embodiments, the second pain reducing agent is an opioid. Other analgesics such as local anesthetics including anticonvulsants and antidepressants are also contemplated.

The pharmaceutical compositions of the invention can be used for the treatment of the disorders as described herein in mammals, including human.

The pharmaceutical compositions of this invention can be administered to humans and other mammals orally, rectally, parenterally, intracisternally, intravaginally, intraperitoneally, topically (as by powders, ointments or drops), bucally or as an oral or nasal spray. The term "parenterally" as used herein, refers to modes of administration which include intravenous, intramuscular, intraperitoneal, intrasternal, subcutaneous and intraarticular injection and infusion.

The term "pharmaceutically acceptable carrier" as used herein, means a non-toxic, inert solid, semi-solid or liquid filler, diluent, encapsulating material or formulation auxiliary of any type. Some examples of materials which can serve as pharmaceutically acceptable carriers are sugars such as, but not limited to, lactose, glucose and sucrose; starches such as, but not limited to, corn starch, and potato starch; cellulose and its derivatives such as, but not limited to, sodium carboxymethyl cellulose, ethyl cellulose and cellulose acetate; powdered tragacanth; malt; gelatin; talc; excipients such as, but not limited to, cocoa butter and suppository waxes; oils such as, but not limited to, peanut oil, cottonseed oil, safflower oil, sesame oil, olive oil, corn oil and soybean oil; glycols; such a propylene glycol; esters such as, but not limited to, ethyl oleate and ethyl laurate; agar; buffering agents such as, but not limited to, magnesium hydroxide and aluminum hydroxide; alginic acid; pyrogen-free water; isotonic saline; Ringer's solution; ethyl alcohol, and phosphate buffer solutions, as well as other non-toxic compatible lubricants such as, but not limited to, sodium lauryl sulfate and magnesium stearate, as well as coloring agents, releasing agents, coating agents, sweetening, flavoring and perfuming agents, preservatives and antioxidants can also be present in the composition, according to the judgment of the formulator.

Pharmaceutical compositions of this invention for parenteral injection comprise pharmaceutically acceptable sterile aqueous or nonaqueous solutions, dispersions, suspensions or emulsions as well as sterile powders for reconstitution into sterile injectable solutions or dispersions just prior to use. Examples of suitable aqueous and nonaqueous carriers, diluents, solvents or vehicles include water, ethanol, polyols (such as glycerol, propylene glycol, polyethylene glycol and the like), vegetable oils (such as olive oil), injectable organic esters (such as ethyl oleate) and suitable mixtures thereof. Proper fluidity can be maintained, for example, by the use of coating materials such as lecithin, by the maintenance of the required particle size in the case of dispersions and by the use of surfactants.

These compositions may also contain adjuvants such as preservatives, wetting agents, emulsifying agents and dispersing agents. Prevention of the action of microorganisms can be ensured by the inclusion of various antibacterial and antifungal agents, for example, paraben, chlorobutanol, phenol sorbic acid and the like. It may also be desirable to include isotonic agents such as sugars, sodium chloride and the like. Prolonged absorption of the injectable pharmaceutical form can be brought about by the inclusion of agents, which delay absorption such as aluminum monostearate and gelatin.

In some cases, in order to prolong the effect of the drug, it is desirable to slow the absorption of the drug from subcutaneous or intramuscular injection. This can be accomplished by the use of a liquid suspension of crystalline or amorphous material with poor water solubility. The rate of absorption, of the drag then depends upon its rate of dissolution which, in turn, may depend, upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such, as polylactide-polyglycolide. Depending upon the ratio of drug to polymer and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissues.

The injectable formulations can be sterilized, for example, by filtration through a bacterial-retaining filter or by incorporating sterilizing agents in the form of sterile solid compositions which can be dissolved or dispersed in sterile water or other sterile injectable medium just prior to use.

Solid dosage forms for oral administration include capsules, tablets, pills, powders and granules. In such solid dosage forms, the active compound may be mixed with at least one inert, pharmaceutically acceptable excipient or carrier, such as sodium citrate or dicalcium phosphate and/or a) fillers or extenders such as starches, lactose, sucrose, glucose, mannitol and silicic acid; b) binders such as carboxymethylcellulose, alginates, gelatin, polyvinylpyrrolidone, sucrose and acacia; c) humectants such as glycerol; d) disintegrating agents such as agar-agar, calcium carbonate, potato or tapioca starch, alginic acid, certain silicates and sodium carbonate; e) solution retarding agents such as paraffin; f) absorption accelerators such as quaternary ammonium compounds; g) wetting agents such as cetyl alcohol and glycerol monostearate; h) absorbents such as kaolin and bentonite clay and i) lubricants such as talc, calcium stearate, magnesium stearate, solid polyethylene glycols, sodium lauryl sulfate and mixtures thereof. In the case of capsules, tablets and pills, the dosage form may also comprise buffering agents.

Solid compositions of a similar type may also be employed as fillers in sort and hard-filled gelatin capsules using such carriers as lactose or milk sugar as well as high molecular weight polyethylene glycols and the like.

The solid dosage forms of tablets, dragees, capsules, pills and granules can be prepared with coatings and shells such as enteric coatings and other coatings well-known in the pharmaceutical formulating art. They may optionally contain opacifying agents and may also be of a composition such that they release the active ingredient(s) only, or preferentially, in a certain part of the intestinal tract, optionally, in a delayed manner. Examples of embedding compositions which can be used include polymeric substances and waxes.

The active compounds can also be in micro-encapsulated form, if appropriate, with one or more of the above-mentioned carriers.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor and sesame oils), glycerol, tetrahydrofurfuryl alcohol, polyethylene glycols and fatty acid esters of sorbitan and mixtures thereof.

Besides inert diluents, the oral compositions may also include adjuvants such as wetting agents, emulsifying and suspending agents, sweetening, flavoring and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar, tragacanth and mixtures thereof.

Composition for rectal or vaginal administration are preferably suppositories which can be prepared by mixing the compounds of this invention with suitable non-irritating carriers or carriers such as cocoa butter, polyethylene glycol or a suppository wax which are solid at room temperature but liquid at body temperature and therefore melt in the rectum or vaginal cavity and release the active compound.

Compounds of the present invention can also be administered in the form of liposomes. As is known in the art, liposomes are generally derived from phospholipids or other lipid substances. Liposomes are formed by mono- of multilamellar hydrated liquid crystals which are dispersed in an aqueous medium. Any non-toxic, physiologically acceptable and metabolizable lipid capable of forming liposomes can be used. The present compositions in liposome form can contain, in addition to a compound of the present invention, stabilizers, preservatives, excipients and the like. The preferred lipids are natural and synthetic phospholipids and phosphatidyl cholines (lecithins) used separately or together.

Methods to form liposomes are known in the art. See, for example, Prescott, Ed., Methods in Cell Biology, Volume XIV, Academic Press, New York, N.Y. (1976), p. 33 et seq.

Dosage forms for topical administration of a compound of this invention include powders, sprays, ointments and inhalants. The active compound may be mixed under sterile conditions with a pharmaceutically acceptable carrier and any needed preservatives, buffers or propellants which may be required. Opthalmic formulations, eye ointments, powders and solutions are also contemplated as being within the scope of this invention.

The compounds of the present Invention can be used in the form of pharmaceutically acceptable salts. The phrase "pharmaceutically acceptable salt" means those salts which are, within the scope of sound medical judgement, suitable for use in contact with the tissues of humans and lower animals without undue toxicity, irritation, allergic response and the like and are commensurate with a reasonable benefit/risk ratio.

Pharmaceutically acceptable salts are well known in the art. For example, S. M. Berge et al. describe pharmaceutically acceptable salts in detail in (J. Pharmaceutical Sciences, 1977, 66; 1 et seq).

The compounds of the invention may contain either a basic or an acidic functionality, or both, and can be converted to a pharmaceutically acceptable salt, when desired, by using a suitable acid or base. The salts can be prepared in situ during the final isolation and purification of the compounds of the invention.

Representative acid addition salts include, but are not limited to acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, fumarate, hydrochloride, hydrobromide, hydroiodide, 2-hydroxyethansulfonate (isothionate), lactate, malate, maleate, methanesulfonate, nicotinate, 2-napthalenesulfonate, oxalate, palmitoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups can be quaternized with such agents as lower alkyl halides such as, but not limited to, methyl, ethyl, propyl, and butyl chlorides, bromides and iodides; dialkyl sulfates like dimethyl, diethyl, dibutyl and diamyl sulfates; long chain halides such as, but not limited to, decyl, lauryl, myristyl and stearyl chlorides, bromides and iodides; arylalkyl halides like benzyl and phenethyl bromides and others. Water or oil-soluble or dispersible products are thereby obtained. Examples of acids which can be employed to form pharmaceutically acceptable acid addition salts include such inorganic acids as hydrochloric acid, hydrohromic acid, sulfuric acid, and phosphoric acid and such organic acids as acetic acid, fumaric acid, maleic acid, 4-methylbenzenesulfonic acid, succinic acid and citric acid.

Basic addition salts can be prepared in situ during the final isolation and purification of compounds of this invention by reacting a carboxylic acid-containing moiety with a suitable base such as, but not limited to, the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as, but not limited to, lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like.

The term "pharmaceutically acceptable prodrug" or "prodrug" as used herein, represents those prodrugs of the compounds of the present invention which are, within the scope of sound medical judgement, suitable for use in contact with the tissues of humans and lower animals without undue toxicity, irritation, allergic response, and the like, commensurate with a reasonable benefit/risk ratio, and effective for their intended use.

The present invention contemplates compounds of formula (I) formed by synthetic means or formed by in vivo biotransformation of a prodrug.

The compounds of the Invention can exist in unsolvated as well as solvated forms, including hydrated forms, such as hemi-hydrates. In general, the solvated forms, with pharmaceutically acceptable solvents such as water and ethanol among others are equivalent to the unsolvated forms for the purposes of the invention.

f. General Synthesis

This invention is intended to encompass compounds of the invention when prepared by synthetic processes or by metabolic processes. Preparation of the compounds of the invention by metabolic processes include those occurring in the human or animal body (in vivo) of processes occurring in vitro.

The synthesis of compounds of general formula (I) wherein the groups $R^1$, $R^2$, $R^3$, $R^f$, $R^g$, $R^w$, m, and Y have the meanings as set forth In the summary section unless otherwise noted, is exemplified in the accompanying Schemes 1-5.

As used in the descriptions of the schemes and the examples, certain abbreviations are intended to have the following meanings: Dibal-H for diisobutylaluminum hydride, DMAP for (4-dimethylamino)pyridine, DMF for N,N-dimethylformamide, DBU for 1,8-diazabicyclo(5.4.0)undec-7-ene, EDCI for 1-(3-dimethylaminopropyl)-3-ethylcarbodiimide hydrochloride, HOBt for 1-hydroxybenzotriazole, NMO for 4-methylmorpholine N-oxide, NMP for N-methylpyrrolidinone, PDC for pyridinium dichromate, $PdCl_2(PPh_3)_2$ for bis(triphenylphosphine)palladium(II) dichloride, $Pd(PPh_3)_4$ for tetrakis(triphenylphosphine)palladium(0), Ph for phenyl, and TPAP for tetrapropylammonium perruthenate.

Compounds of general formula (I) wherein Y is $-OR^f$ group can be prepared using general procedures as illustrated in Scheme 1.

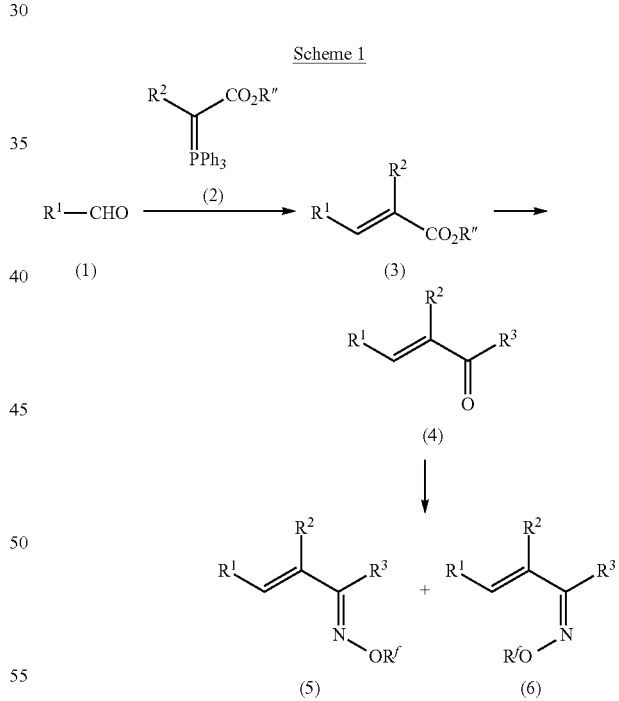

Aldehydes of general formula (1) can be reacted with phosphorus ylides of general formula (2) wherein R″ is alkyl, in a solvent such as toluene at refluxing temperatures to provide unsaturated esters of general formula (3) (Adam, W. et al., Journal of Organic Chemistry 2002, 67, 8395-8399). The conversion of compound (3) to (4) is a stepwise reaction sequence comprising; (a) reduction of (3) to the corresponding aldehyde using a reagent such as diisobutylaluminum hydride or lithium aluminum hydride, (b) addition of an organometallic nucleophile in the form of a Grignard or organolithium reagent, and (c) conversion of the product from step (b) to the corresponding ketone derivative using an oxidizing reagent such as tetrapropylammonium perruthenate (Ley, S. V. et. al. Synthesis 1994, 7, 639-966) or pyridinium dichromate (PDC). Step (b) can be carried out in a solvent such as tetrahydrofuran or diethyl ether at a temperature ranging from about −78° C. to about 0° C. The crude products from both steps (a) and (b) can be isolated and subjected to the subsequent step with or without purification. Step (c) can be carried out using a variety of oxidizing agents known to those skilled in the art in nonpolar solvents such as dichloromethane typically at ambient temperatures. Condensation of ketone (4) with hydrochloride salt of hydroxylamine or alkoxyamine of formula $R^fONH_2$ wherein $R^f$ is hydrogen or alkyl, in the presence of a base such as but not limited to triethylamine in a solvent such as benzene or tetrahydrofuran at a temperature ranging from about 25° C. to about 80° C., provides oximes of general formula (5) or (6). Compounds (5) and (6) are geometrical isomers which may be separated and purified by standard chromatographic methods familiar to those skilled in the art.

Alternatively, ketone (4) can be prepared employing general procedures as illustrated in Scheme 2.

tetrahydrofuran at a temperature ranging from about −20° C. to about 0° C.

Treatement of (7) with Grignard reagents of formula $R^3MgX^{101}$ wherein $X^{101}$ is Cl or Br, in a solvent such as tetrahydrofuran at a temperature ranging from about −78° C. to about 0° C. provides ketones of general formula (4).

Intermediate (7) can also be prepared according to the synthetic sequence as shown in Scheme 3. Ester (3) can be saponified to carboxylic acid (8) using reagents such as lithium or potassium hydroxide in aqueous solution at ambient temperature using a co-solvents including but not limited to tetrahydrofuran and ethanol. Carboxylic acid (8) can be reacted with N-methoxy-N-methylamine hydrochloride (Basha, A. et al. Tetrahedron Letters 1977, 48, 4171-4174), using dehydrative coupling reagents such as EDCI in combination with HOBt or DMAP (Montalbetti, C. A. G. N. Tetrahedron 2005, 61 10827-10852), and a base such as But not limited to triethylamine. These reactions are carried out in a solvent such as toluene or dichloromethane at a temperature ranging from about 0° C. to about 25° C. to provide amides of general formula (7).

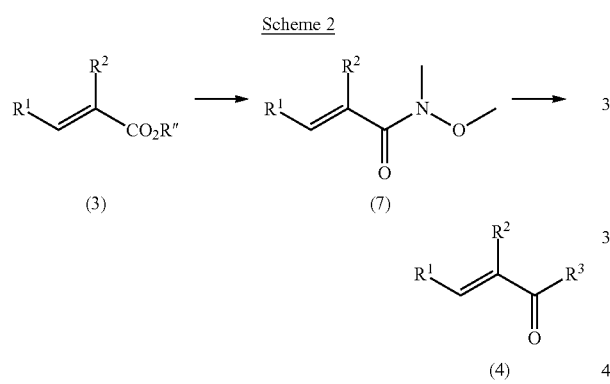

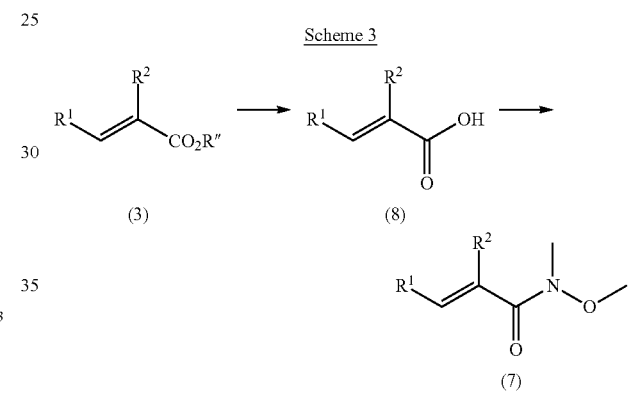

Unsaturated esters of general formula (3), prepared according to the methods of Scheme 1 or Scheme 3, can be reacted with N-methoxy-N-methylamide hydrochloride and trimethylaluminum (Lipton, M. F. et al., Organic Syntheses 1980, 59, 49-53) in a solvent such as toluene or dichloromethane at a temperature ranging from about −40° C. to about 25° C. to provide amides of general formula (7). Alternatively, (7) can be prepared by reacting (3) with N-methoxy-N-methylamine hydrochloride and isopropylmagnesium chloride (Williams, J. M. et al., Tetrahedron Letters 1995, 36(31), 5461-5464) in a solvent such as Alternatively, unsaturated esters of formula (3) may be prepared according to the procedures as described in Scheme 4.

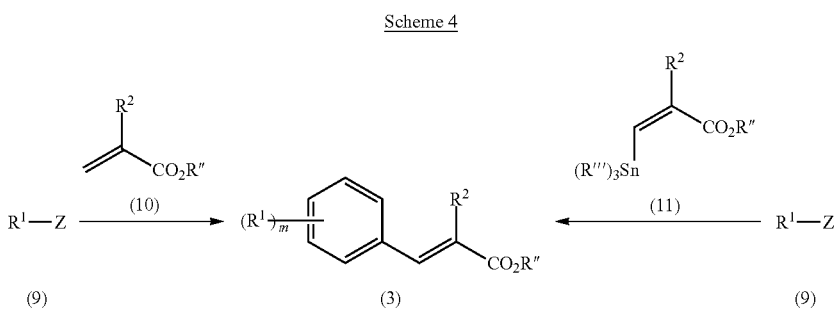

Heteroaryl halides of general formula (9) wherein the Z group is a chlorine, bromine, or iodine atom may be reacted with unsaturated esters of formula (10) in the presence of a palladium catalyst such as but not limited to palladium(II) acetate to generate (3) (Knowles, J. P. Organic & Biomolecular Chemistry 2007, 5, 31-44). These reactions are generally performed using an amine base such as but not limited to diisopropylethylamine or DBU, in a solvent such as acetonitrile or toluene, or DMF, at temperatures ranging from about 50° C. to about 100° C. A related approach tor the synthesis of unsaturated esters of general formula (3) from (9) involves reaction with substituted, alkenes of general formula (11) wherein R''' is alkyl. In this case, the substituted alkene (11) contains a trialkyltin moiety such as trimethylstannyl or tributylstannyl (Yin, L. et al., Chemical Reviews 2007, 107, 133-173). These reactions are generally performed in the presence of catalytic quantities of a palladium(II) or palladium (0) reagent, such as dichloropalladium bis(triphenylphosphine) or tetrakis(triphenylphosphine)palladium, respectively, in polar aprotic solvents such as DMF or NMP at temperatures ranging from about 25° C. to about 125° C.

Compounds of general formula (1) wherein Y is $NR^fR^g$ can be prepared using general procedures as illustrated in Scheme 5.

Scheme 5

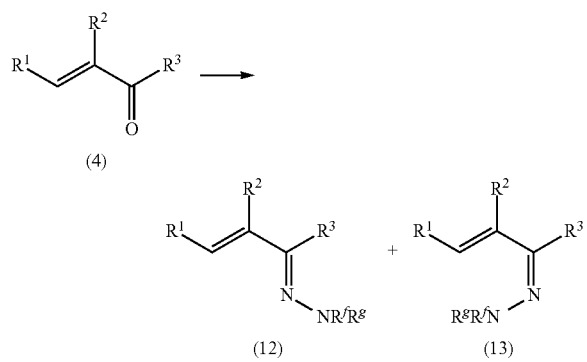

Reaction of ketone (4), prepared according to the methods illustrated in Schemes 1 and 2 with substituted hydrazines of general formula $R^fR^gNNH_2$ is a solvent such as benzene or tetrahydrofuran at a temperature ranging from about 0° C. to about 80° C. provides hydrazones of general formula (12) or (13). Compounds (12) and (13) are geometrical isomers which may be separated and purified by standard chromatographic methods familiar to those skilled in the art.

It will be appreciated that the synthetic schemes and specific examples as illustrated in the Examples section are illustrative and are not to be read as limiting the scope of the invention as it is defined in the appended claims. All alternatives, modifications, and equivalents of the synthetic methods and specific examples are included within the scope of the claims.

Optimum reaction conditions and reaction times for each individual step may vary depending on the particular reactants employed and substituents present in the reactants used. Unless otherwise specified, solvents, temperatures and other reaction conditions may be readily selected by one of ordinary skill in the art. Specific procedures are provided in the Synthetic Examples section. Reactions may be worked up in the conventional manner, e.g. by eliminating the solvent from the residue and further purified according to methodologies generally known in the art such as, but not limited to, crystallization, distillation, extraction, trituration and chromatography. Unless otherwise described, the starting materials and reagents are either commercially available or may be prepared by one skilled in the art from commercially available materials using methods described in the chemical literature.

Routine experimentations, including appropriate manipulation of the reaction conditions, reagents and sequence of the synthetic route, protection of any chemical functionality that may not be compatible with the reaction conditions, and deprotection at a suitable point in the reaction sequence of the method are included in the scope of the invention. Suitable protecting group and the methods for protecting and deprotecting different substituents using such suitable protecting groups are well known to those skilled in the art; examples of which may be found in T. Greene and P. Wuts, Protecting Groups in Chemical Synthesis (3$^{rd}$ ed.), John Wiley & Sons, NY (1999), which is incorporated herein by reference in its entirety. Synthesis of the compounds of the invention may be accomplished by methods analogous to those described in the synthetic schemes described hereinabove and in specific examples.

Starting materials, if not commercially available, may be prepared by procedures selected from standard organic chemical techniques, techniques that are analogous to the synthesis of known, structurally similar compounds, or techniques that are analogous to the above described schemes or the procedures described in the synthetic examples section.

When an optically active form of a compound of the invention is required, it may be obtained by carrying out one of the procedures described herein using an optically active starting material (prepared, for example, by asymmetric induction of a suitable reaction step), or by resolution of a mixture of the stereoisomers of the compound or intermediates using a standard procedure (such as chromatographic separation, recrystallization or enzymatic resolution).

Similarly, when a pure geometric isomer of a compound of the invention is required, it may be obtained by carrying out one of the above procedures using a pure geometric isomer as a starting material, or by resolution of a mixture of the geometric isomers of the compound or intermediates using a standard procedure such as chromatographic separation.

g. Examples

Examples 1-11 were prepared using general procedures as outlined in the following:

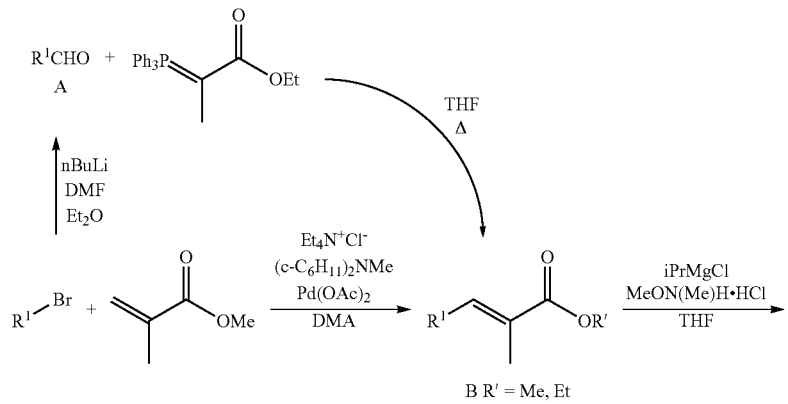

-continued

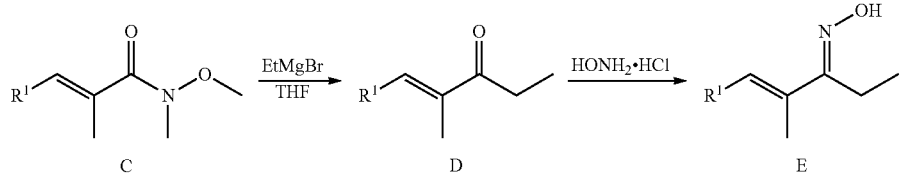

Example A

Heteroaryl aldehydes

Under a $N_2$ atmosphere, n-BuLi (1.0 eq) was added to a stirred mixture of an appropriate heteroaryl halide (1.0 eq) in diethyl ether (50 mL) at −78° C. The reaction mixture was stirred for 30 min at −78° C. and then DMF (1.3 eq) was added. The mixture was stirred for 1 hr during which the reaction was allowed to warm to room temperature. The reaction mixture was poured into 5% aq $K_2CO_3$ solution and the product was extracted with ethyl acetate (4×50 mL). The combined organic layers were washed with brine, dried, and concentrated. The crude product was purified by chromatography on silica gel using petroleum ether/ethyl acetate (about 10:1 to about 4:1) to afford the title compounds (yield 15%-30%).

Example B

(E)-(methyl or ethyl)-2-methyl-3-heteroaryl)acrylates

Method A

To a solution of Example A (1.0 eq) in dry THF (20 mL) at room temperature was added (1-ethoxycarbonylethylidene)triphenylphosphorane (1.0 eq). The reaction mixture wax stirred at 60° C. under a $N_2$ atmosphere for 3 hours. The reaction mixture was cooled to room temperature and the solvent removed. The residue was suspended in petroleum ether, and the resulting solid was filtered and washed with petroleum ether. The filtrate was then concentrated to obtain (E)-ethyl-2-methyl-3-(heteroaryl)acrylate (yield 40%-70%).

Method B

To a stirred solution of an appropriate heteroaryl halide (1.0 eq) in dimethylacetamide (20 mL) was added methyl methacrylate (1.1 eq), tetraethylammonium chloride (1.1 eq), N-cyclohexyl-N-methylcyclohexanamine (1.5 eq) and palladium(II) acetate (0.02 eq). The reaction mixture was heated at 100° C. under a $N_2$ atmosphere overnight. The reaction mixture was then cooled to room temperature, diluted with ethyl acetate, and washed with water and brine. The separated organic phase was dried over $Na_2SO_4$, filtered, and evaporated. The crude product was purified by flash column chromatography, eluted with petroleum ether/ethyl acetate, to afford (E)-methyl-2-methyl-3-(heteroaryl) acrylate (yield 20-70%).

Example C

(E)-N-methoxy-N,2-dimethyl-3-(heteroaryl)acrylamides

Example B (1.0 eq) and N-methoxy-N-methylamine hydrochloride (1.55 eq) were slurried in 20 mL of THF and cooled to −20° C. under a $N_2$ atmosphere. A solution of isopropylmagnesium chloride (2.0 M in THF, 1.5 eq) was added over 15 min, maintaining the temperature below −5° C. The mixture was stirred for 30 min at −10° C. and quenched with 20% wt aqueous $NH_4Cl$ solution. The mixture was extracted with ethyl acetate and the organic layer was dried over $Na_2SO_4$, filtered, and concentrated to obtain the title compounds.

Example D

(E)-2-methyl-1-(heteroaryl)pent-1-en-3-ones

To a solution of Example C (1.0 eq) in THF (20 mL) was added ethylmagnesium bromide (3.0 M, 3 eq) under a $N_2$ atmosphere at about −20° C. The mixture was stirred for 1.5 hour at about −10° C. and then quenched with 20% wt aqueous $NH_4Cl$ solution. After warming to room temperature, the two phases were separated and the aqueous phase was extracted with ethyl acetate. The combined organic extract was washed with brine, dried over $Na_2SO_4$, and concentrated. The residue was purified by flash column chromatography and concentrated to afford the title compounds, yield 15-40%.

Example E

(1E,3E)-2-methyl-1-arylpent-1-en-3-one oximes

To a solution, of Example D (1.0 eq) in ethanol (5 mL) was added $HONH_2 \cdot HCl$ (1.2 eq) and sodium acetate (1.5 eq). The reaction mixture was stirred at room temperature overnight. After removal of the solvent, the residue was extracted with ethyl acetate and washed with water, dried over $Na_2SO_4$, and concentrated. The crude product was purified by Prep-TLC to afford the title compounds, yield 10-40%.

Example 1

(1E,3E)-1-(6-fluoropyridin-3-yl)-2-methylpent-1-en-3-one oxime

The title compound was prepared according to the general procedures, starting with 5-bromo-2-fluoropyridine and methyl methacrylate. $^1$H NMR (300 MHz, DMSO-$d_6$) δ 11.18(s, 1H), 8.25 (d, J=2.1 Hz, 1H), 8.00 (td, J=8.3, 2.5 Hz, 1H), 7.21 (dd, J=8.5, 2.9 Hz, 1H), 6.90 (s, 1H), 2.62 (q, J=7.5 Hz, 2H), 1.99 (s, 3H), 1.05 (t, J=7.5 Hz, 3H); MS (DCI$^+$) 209(M+H)$^+$.

Example 2

(1E,3E)-2-methyl-1-thien-2-ylpent-1-en-3-one oxime

The title compound was prepared according to the general procedures, starting with 2-bromothiophene and methyl methacrylate. $^1$H NMR. (300 MHZ, DMSO-$d_6$) δ 11.11 (d, J=3.3 Hz, 1H), 7.62 (d, J=5.0 Hz, 1H), 7.29 (d, J=3.4 Hz, 1H), 7.13 (dd, J=5.1, 3.6 Hz, 1H), 7.10 (s, 1H), 2.60 (q, J=7.5 Hz, 2H), 2.14 (d, J=0.8 Hz, 3H), 1.02 (t, J=7.5 Hz, 3H); MS (DCI$^+$) 196 (M+H)$^+$.

Example 3

(1E,3E)-1-(6-methoxypyridin-3-yl)-2-methylpent-1-en-3-one oxime

The title compound was prepared according to the general procedures, starting with 5-bromo-2-methoxypyridine and methyl methacrylate. $^1$H NMR (300 MHz, DMSO-d$_6$) δ 11.06(s, 1H), 8.20 (d, J=2.4 Hz, 1H), 7.74 (dd, J=8.6, 2.4 Hz, 1H), 6.88-6.79 (m, 2H), 3.87 (s, 3H), 2.61 (q, J=7.5 Hz, 2H), 2.00 (d, J=1.0 Hz, 3H), 1.05 (t, J=7.5 Hz, 3H); MS (DCI$^+$) 221 (M+H)$^+$.

Example 4

(1E,3E)-2-methyl-1-thien-3-ylpent-1-en-3-one oxime

The title compound was prepared according to the general procedures, starting with 3-bromothiophene and methyl methacrylate. $^1$H NMR (300 MHz, DMSO-d$_6$) δ 11.02 (s, 1H), 7.58-7.53 (m, 2H) 7.26 (dd, J=4.3, 2.0 Hz, 1H), 6.86 (d, J=1.0 Hz, 1H), 2.58 (q, J=7.5Hz, 2H), 2.07 (d, J=1.0 Hz, 3H), 1.03 (t, J=7.5 Hz, 3H); MS (DCI$^+$) 196 (M+H)$^+$, Example 5

(1E,3E)-2-methyl-1-pyridin-3-ylpent-1-en-3-one oxime

The title compound was prepared according to the general procedures, starting with 3-bromopyridine and methyl methacrylate. $^1$H NMR (500 MHz, DMSO/D$_2$O) δ 8.57 (br s, 1H), 8.48-8.43 (m, 1H), 7.82 (dd, J=7.9, 2.1 Hz, 1H), 7.44 (dd, J=7.9, 4.8 Hz, 1H), 6.91 (s, 1H), 2.63 (q, J=7.5 Hz, 2HHh), 2.01 (d, J=1.2 Hz, 3H), 1.10-1.01 (m, 3H); MS (DCI$^+$) 191(M+H)$^+$.

Example 6

(1E,3E)-2-methyl-1-pyridin-4-ylpent-1-en-3-one oxime

The title compound was prepared according to the general procedures, starting with 4-bromopyridine and 1-ethoxycarbonylethylidene)triphenylphosphorane, $^1$H NMR (500 MHz, DMSO/D$_2$O) δ 8.58-8.53 (m, 2H), 7.41-7.36 (m, 2H), 6.87 (s, 1H), 2.62 (q, J=7.5 Hz, 2H), 2.03 (d, J=1.2 Hz, 3H), 1.05 (t, J=7.5 Hz, 3H); MS (ESI$^+$) 191 (M+H)$^+$.

Example 7

(1E,3E)-2-methyl-1-(6-methylpyridin-3-yl)pent-1-en-3-one oxime

The title compound was prepared according to the general procedures, starting with 5-bromo-2-methylpyridine and methyl methacrylate. $^1$H NMR (300 MHz, DMSO-d$_6$) δ 11.12 (s, 1H), 8.45 (d, J=2.0 Hz, 1H), 7.68 (dd, J=8.1, 2.3 Hz, 1H), 7.26 (d, J=8.0 Hz, 1H), 6.86 (s, 1H), 2.61 (q, J=7.5 Hz, 2H), 2.47 (s, 3H), 2.00 (s, 3H), 1.05 (t, J=7.5 Hz, 3H); MS (DCI$^+$) 205 (M+H)$^+$.

Example 8

(1E,3E)-2-methyl-1-quinolin-3-ylpent-1-en-3-one oxime

The title compound was prepared according to the general procedures, starting with 3-bromoquinoline and methyl methacrylate, $^1$H NMR (500 MHz, DMSO/D$_2$O) δ 8.92 (d, J=2.2 Hz, 1H), 8.38 (d, J=2.1 Hz, 1H), 8.06-8.00 (m, 2H), 7.78 (ddd, J=8.4, 6.9, 1.5 Hz, 1H), 7.68-7.61 (m, 1H), 7.10 (s, 1H), 2.69 (q, J=7.5 Hz, 2H), 2.12 (d, J=1.1 Hz, 3H), 1.11 (t, J=7.5 Hz, 3H); MS (DCI$^+$) 241 (M+H)$^+$.

Example 9

(1E,3E)-2-methyl-1-(4-methylpyridin-3-yl)pent-1-en-3-one oxime

The title compound was prepared according to the general procedures, starting with 3-bromo-4-methylpyridine and methyl methacrylate. $^1$H NMR (500 MHz, DMSO/D$_2$O) δ 8.38-8.28 (m, 2H), 7.31 (d, J=4.9 Hz, 1H), 6.86 (s, 1H), 2.64 (q, J=7.5 Hz, 2H), 2.25 (s, 3H), 1.83 (d, J=1.1 Hz, 3H), 1.08 (t, J=7.5 Hz, 3H); MS (ESI$^+$) 205 (M+H)$^+$.

Example 10

(1E,3E)-2-methyl-1-[6-(trifluoromethyl)pyridin-3-yl]pent-1-en-3-one oxime

The title compound was prepared according to the general procedures, starting with 5-bromo-2-(trifluoromethyl)pyridine and methyl methacrylate. $^1$NMR (500 MHz, DMSO/D$_2$O) δ 8.92-8.83 (m, 2H), 8.18 (s, 1H), 7.00 (s, 1H), 2.64 (q, J=7.6 Hz, 2H), 2.03(d, J=0.7 Hz, 3H), 1.07 (t, J=7.5 Hz, 3H); MS (DCI$^+$) 259 (M+H)$^+$.

Example 11

(1E,3E)-1-(isoquinolin-4-yl)-2-methylpent-1-en-3-one oxime

The title compound was prepared according to the general procedures, starting with 4-bromoisoquinoline and methyl methacrylate. $^1$H NMR (500 MHz, CDCl$_3$) δ 9.22 (s, 1H), 8.44 (s, 1H), 8.08 (s, 1H), 8.02-8.04 (m, 1H), 7.87-7.89 (m, 1H), 7.72-7.77 (m, 1H), 7.64-7.68 (m, 1H), 7.22 (s, 1H), 2.83 (q, J=7.5 Hz, 2H), 1.95 (s, 3H), 1.28 (t, J=7.5 Hz, 3H); MS (DCI$^+$) 241 (M+H)$^+$.

It is understood that the foregoing detailed description and accompanying examples are merely illustrative and are not to be taken as limitations upon the scope of the invention, which is defined solely by the appended claims and their equivalents. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof.

The invention claimed is:

1. A method for treating pain in a subject in need of such treatment, comprising administering therapeutically effective amount of one or more compounds selected from the group consisting of (1E,3E)-1-(6-fluoropyridin-3-yl)-2-methylpent-1-en-3-one Oxime, (1E,3E)-2-methyl-1-thien-2-ylpent-1-en-3-one Oxime, (1E,3E)-1-(6-methoxypyridin-3- yl)-2-methylpent-1-en-3-one Oxime, (1E,3E)-2-methyl-1-thien-3-ylpent-1-en-3-one Oxime, (1E,3E)-2-methyl-1-pyridin-3-ylpent-1-en-3-one Oxime, (1E,3E)-2-methyl-1-pyridin-4-ylpent-1-en-3-one Oxime, (1E,3E)-2-methyl-1-(6-methylpyridin-3-yl)pent-1-en-3-one Oxime, (1E,3E)-2-methyl-1-quinolin-3-ylpent-1-en-3-one Oxime, (1E,3E)-2-methyl-1-(4-methylpyridin-3-yl)pent-1-en-3-one Oxime, (1E,3E)-2-methyl-1-[6-(trifluoromethyl)pyridine-3-yl]pent-1-en-3-one Oxime, (1E,3E)-1-(isoquinolin-4-yl)-2-methyl-pent-1-en-3-one Oxime and mixtures thereof.

2. The method of claim 1 further comprising the step of co-administering with one or more second pain reducing agent.

3. The method of claim 2 wherein the second pain reducing agent is acetaminophen or a nonsteroidal anti-inflammatory drug, or combination thereof.

4. The method of claim 3 wherein the nonsteroidal anti-inflammatory drug is ibuprofen.

\* \* \* \* \*